US007245388B2

(12) United States Patent
Isozaki et al.

(10) Patent No.: US 7,245,388 B2
(45) Date of Patent: Jul. 17, 2007

(54) METHOD AND DEVICE FOR SURFACE INSPECTION

(75) Inventors: Hisashi Isozaki, Tokyo-to (JP); Takuji Sato, Tokyo-to (JP); Yoshiyuki Enomoto, Tokyo-to (JP); Hiroyuki Maekawa, Tokyo-to (JP)

(73) Assignee: Kabushiki Kaisha Topcon, Tokyo-to (JP)

( * ) Notice: Subject to any disclaimer, the term of this patent is extended or adjusted under 35 U.S.C. 154(b) by 403 days.

(21) Appl. No.: 10/732,064

(22) Filed: Dec. 10, 2003

(65) Prior Publication Data
US 2004/0119971 A1 Jun. 24, 2004

(30) Foreign Application Priority Data
Dec. 20, 2002 (JP) ............... 2002-370946

(51) Int. Cl.
G01B 11/28 (2006.01)

(52) U.S. Cl. .................... 356/630; 356/237.5

(58) Field of Classification Search ............ None
See application file for complete search history.

(56) References Cited

U.S. PATENT DOCUMENTS

| 5,179,422 A * | 1/1993 | Peterson ............... 356/237.1 |
| 6,104,481 A * | 8/2000 | Sekine et al. ........... 356/237.2 |
| 6,731,384 B2 * | 5/2004 | Ohshima et al. ........ 356/237.2 |
| 6,940,604 B2 * | 9/2005 | Jung et al. .............. 356/503 |
| 7,050,178 B2 * | 5/2006 | Morath et al. .......... 356/630 |

* cited by examiner

Primary Examiner—Layla G. Lauchman
Assistant Examiner—Juan D. Valentin, II
(74) Attorney, Agent, or Firm—Nields & Lemack

(57) ABSTRACT

A method for surface inspection, comprising the step of projecting at least two laser beams with different wavelengths to a same point to be inspected via a same projecting lens, the step of setting incident angles of the two laser beams so that fluctuations of values of reflectivity of the laser beams are complementary to each other, and the step of detecting reflected scattered light components.

16 Claims, 4 Drawing Sheets

415nm: θ = 74.6d/395nm: θ = 64.5d

415nm: θ = 64.5d/395nm: θ = 74.6d

METHOD AND DEVICE FOR SURFACE INSPECTION

BACKGROUND OF THE INVENTION

The present invention relates to a method and a device for surface inspection for inspecting very small foreign objects on a surface of a substrate such as a semiconductor wafer or for checking micro-size flaws such as crystal defects.

In a manufacturing process of semiconductor devices, very small foreign objects are often attached to a surface of a substrate such as a wafer, and this exerts serious influence on product quality and yield. For this reason, surface inspection is performed on the surface of the substrate in the process to manufacture semiconductor devices. Semiconductor devices are now produced with increasingly higher density, and the manufacturing process is also complicated. As a result, diverse types of films are formed on the surface of the wafer.

In the surface inspection device, an inspection light is projected to the substrate surface, and reflected scattered light components caused by foreign objects are received by a detector. Thus, the foreign objects are detected. In order to attain higher detection accuracy in the surface inspection, it is necessary to maintain an S/N ratio to detect and distinguish the foreign objects. For this purpose, it is necessary to set inspection conditions, under which the reflected scattered light components from the foreign objects have a sufficiently high light amount.

A wavelength and intensity of the detection light projected to the substrate surface is related to detection sensitivity and detection accuracy. By shortening the wavelength, the detection sensitivity can be improved. By attaining sufficient intensity of the reflected scattered light components, it is possible to increase an S/N ratio in the detection and to improve detection accuracy.

Referring to FIG. 5, description will be given below on general features of a conventional type surface inspection device.

In the figure, reference numeral 1 denotes a light source unit, 2 is a projecting optical system, 3 is a photodetection unit, 4 is a rotary driving unit, 5 is a substrate such as a wafer to be inspected, and 6 is a control unit.

The rotary driving unit 4 comprises a rotary motor 7 and a rotary table 8 rotated by the rotary motor 7. The substrate 5 is fixed on the rotary table 8, and the rotary motor 7 is controlled so as to be rotated at a constant speed with a predetermined number of revolutions by a driving unit 9 based on a command from the control unit 6.

The light source unit 1 comprises a first laser emitting unit 11 and a second laser emitting unit 12 for emitting laser beams with a wavelength $\lambda 1$ and a wavelength $\lambda 2$ respectively. As emitters used in the first laser emitting unit 11 and the second laser emitting unit 12, a laser diode (LD) is generally used, which is easy to handle and is advantageous in terms of safety and long service life.

Laser beams emitted from the light source unit 1 are projected to the substrate 5 via the projecting optical system 2. The projecting optical system 2 comprises a first mirror 13 for guiding the laser beam with the wavelength of $\lambda 1$ emitted from the first laser emitting unit 11 toward a lens unit 15, a second mirror 14 for guiding the laser beam with the wavelength of $\lambda 2$ emitted from the second laser emitting unit 12 toward the lens unit 15, and a third mirror 16 and a fourth mirror 17 for projecting the laser beams from the lens unit 15 toward a point to be inspected on the substrate 5.

The first mirror 13 allows the laser beam with the wavelength $\lambda 1$ from the first laser emitting unit 11 to pass and reflects laser beams with other wavelengths. The second mirror 14 reflects the laser beam with the wavelength $\lambda 2$ from the second laser emitting unit 12. Then, this laser beam with the wavelength $\lambda 2$ is allowed to enter the first mirror 13 so that it runs along the same optical axis as the laser beam of the wavelength $\lambda 1$. The lens unit 15 adjusts the flux condition of the laser beams so that the laser beam from the first laser emitting unit 11 and the second laser emitting unit 12 are converged at the point to be inspected.

When the laser beam is projected to the substrate 5, reflected scattered light components are caused by foreign objects, flaws, etc. and the reflected scattered light components are detected by a photodetector 18. Then, data are inputted to the control unit 6 via a signal processor 19.

Depending on the size of the foreign object to be detected, either the first laser emitting unit 11 or the second laser emitting unit 12 of the light source unit 1 is selected by the control unit 6, and the laser beam is emitted. The laser beam is projected to the point to be inspected via the projecting optical system 2.

The control unit 6 rotates the substrate 5 at a constant speed by the rotary motor 7 via the driving unit 9. Then, a projecting position is shifted in a radial direction by a scanning unit (not shown), and the laser beam is controlled so that the laser beams scan spirally over the entire surface of the substrate 5.

The reflected scattered light components detected by the photodetector 18 are produced as an electrical signal. At the signal processor 19, signal processing such as amplification, removal of noise, A/D conversion, etc. is performed on the electrical signal, and then it is inputted to the control unit 6. Based on the signal from the signal processor 19, the control unit 6 detects foreign objects, flaws, defects, etc. Then, a position and a number, etc. of the foreign objects are calculated. These are recorded in a storage unit (not shown) as detection results, or inspection results are displayed on a display unit (not shown).

As the device for surface inspection, for example, those described in JP-B-8-20371 and JP-A-2000-294610 are known.

As described above, the detection sensitivity and detection accuracy in the surface inspection are influenced by intensity, i.e. a light amount, of the reflected scattered light components as detected. However, on a surface of an object to be inspected, which has light transmissivity, reflection characteristics on the surface, i.e. an important factor of the reflected scattered light components, are changed according to a thickness or a type of a film formed on the substrate surface.

For instance, when an inspection light having a certain wavelength is projected to a substrate where a same type of film is formed, reflectivity of the surface is periodically fluctuated according to the change of the thickness of the film formed on the surface. In a specific film thickness, there may be possibility that the detection accuracy to detect foreign objects or defects may be extremely decreased.

For this reason, reflectivity is extremely decreased under a certain condition depending upon the wavelength of the laser beam emitted from the light source in the surface inspection device components, i.e. the value of the wavelength of the laser beam used for the inspection, and also upon the thickness of the film formed on the substrate to be inspected. As a result, intensity of the reflected scattered light components, i.e. the value of the light amount to be detected, is extremely decreased, and this exerts influence on the accuracy of the surface inspection. For instance, when inspection is performed on substrates, which are different in film thickness even though which have the same film type, or under inspection condition where film thickness varies on the same substrate, fluctuation of reflectivity, i.e. variation in intensity and the light amount of the reflected scattered light components, occurs. This gives influences on the accuracy of the surface inspection, and the perfect inspection cannot be performed.

On the other hand, when laser beams with different wavelengths are used at the same time, extreme decrease of the intensity of the reflected scattered light components can be prevented. However, peak values of intensity of the reflected scattered light caused by the change of film thickness vary extremely in each wavelength. Dynamic range of the detection sensitivity must be set to wider range, and this increases the influence from other causes such as noise. On the other hand, the reflectivity varies according to the type of the film formed on the surface, and the type of the film also exerts influence on the detection accuracy.

SUMMARY OF THE INVENTION

It is an object of the present invention to provide a surface inspection method and device for surface inspection, by which, even to an object to be inspected which has different film type and different film thickness and which has optical transmissivity, it is possible to suppress variation in detection accuracy caused by extreme fluctuation of intensity and a light amount of reflected scattered light, and it is possible to perform surface inspection with high accuracy without being influenced by the type and the thickness of the film.

To attain the above object, the method for surface inspection according to the present invention comprises the step of projecting at least two laser beams with different wavelengths to a same point to be inspected via a same projecting lens, the step of setting incident angles of the two laser beams so that fluctuations of values of reflectivity of the laser beams are complementary to each other, and the step of detecting reflected scattered light components. Also, the present invention provides the method for surface inspection as described above, wherein the at least two laser beams have different incident angles with respect to the point to be inspected. Further, the present invention provides the method for surface inspection as described above, wherein wavelengths of the at least two laser beams are 395 nm and 415 nm respectively. Also, the present invention provides the method for surface inspection as described above, wherein an incident angle of the laser beam with wavelength of 395 nm is 64.5° and an incident angle of the laser beam with wavelength of 415 nm is 74.6°. Further, the present invention provides the method for surface inspection as described above, wherein the incident angles are set based on the wavelengths of the each laser beams and to a thickness of a film formed on the point to be inspected. Also, the present invention provides the method for surface inspection as described above, wherein the incident angle of each of the laser beams is set according to a type of the film formed on the point to be inspected. Further, the present invention provides the method for surface inspection as described above, wherein the at least two laser beams are projected at the same time and the reflected scattered light components of the two laser beams are detected. Also, the present invention provides the method for surface inspection as described above, wherein the at least two laser beams are projected at the same time, the reflected scattered light components of the two laser beams each are separately detected from the reflected scattered light components of the two laser beams by an optical separating means, and a component with higher detection value is regarded as a detection light. Further, the present invention provides the method for surface inspection as described above, wherein the at least two laser beams are projected alternately, the reflected scattered light components of the two laser beams each are separately detected, and a component with higher detection value is regarded as a detection light. Also, the present invention provides the method for surface inspection as described above, wherein the incident angle of each of the laser beams is respectively determined according to type of the film formed on the substrate.

The present invention also provides a device for surface inspection, which comprises at least two laser emitting units for emitting two or more laser beams with different wavelengths independently from each other, a projecting lens for projecting the laser beams to a surface of a substrate, and a projecting optical system for projecting the laser beams in parallel to the projecting lens, wherein an incident angle of each of the laser beams to the substrate surface is set by adjusting an incident position of each of the laser beams to the projecting lens. Also, the present invention provides the device for surface inspection as described above, wherein the incident position of each of the laser beams to the projecting lens is set in such manner that fluctuations of values of reflectivity on the substrate surface of each of the laser beams are complementary to each other. Further, the present invention provides the device for surface inspection as described above, wherein a memory unit for storing relevant data relating to incident angles of two or more laser beams with different wavelengths and to reflectivity on a substrate surface, wherein the relevant data is referred depending on a substrate to be inspected, and the incident angle is set so that fluctuations of reflectivity of each of the laser beams on the substrate surface are complementary to each other. Also, the present invention provides the device for surface inspection as described above, wherein the device comprises a wavelength separating optical means, reflected scattered light component corresponding to each laser beam is detected from reflected scattered light components and is compared when two or more different laser beams are projected at the same time, and a reflected scattered light component with a higher comparison value is detected as a detection light. Further, the present invention provides the device for surface inspection as described above, wherein the projecting optical system comprises an optical path switching means, a projection laser beam is selectively projected by the switching of optical path by the optical switching means, reflected scattered light components of each of the laser beams are separately detected, the each reflected scattered light components are compared with each other, and a reflected scattered light component with a higher comparison value is detected as a detection light. Also, the present invention provides the device for surface inspection as described above, wherein wavelengths of the two or more laser beams are 395 nm and 415 nm respectively. Further, the present invention provides the device for surface inspection as described above, wherein the incident angle of the laser beam with a wavelength of 395 nm is 64.5° and the incident angle of the laser beam with a wavelength of 415 nm is 74.6°.

DETAILED DESCRIPTION OF THE PREFERRED EMBODIMENT

Figure 1:
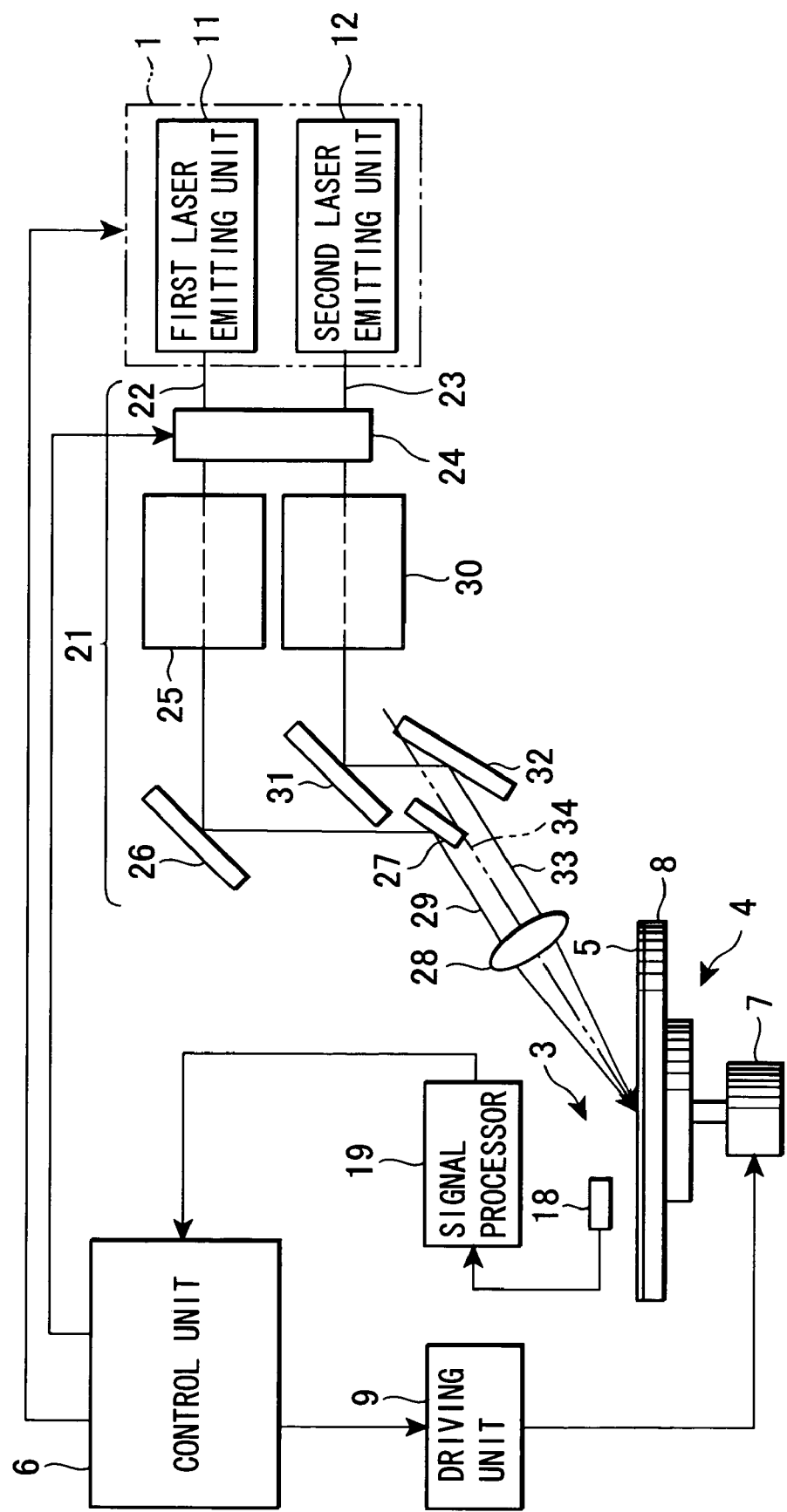
FIG. 1 is a schematical block diagram showing an embodiment of the present invention.

Description will be given below on an embodiment of the present invention referring to the drawings.

Referring to FIG. 1, general features of a surface inspection device according to the present invention will be described.

Figure 5:
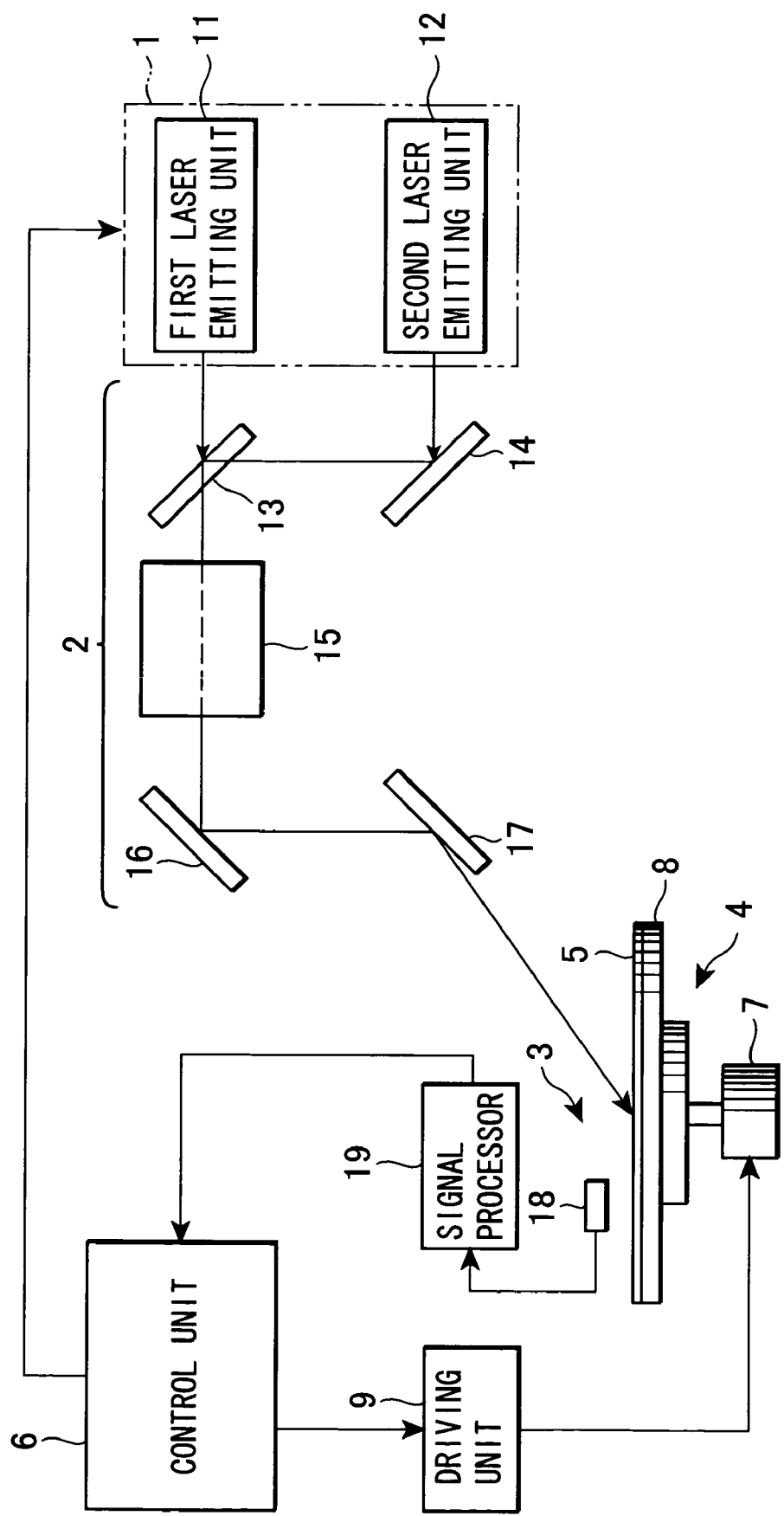
FIG. 5 is a schematical block diagram showing a conventional example.

In FIG. 1, the same component as shown in FIG. 5 is referred by the same symbol, and detailed description is not given here.

The surface inspection device primarily comprises a light source unit 1, a projecting optical system 21, a photodetection unit 3, a rotary driving unit 4, a control unit 6, etc.

The light source unit 1 comprises a laser emitting unit 11 for emitting a first laser beam 22 with a wavelength $\lambda 1$ and a second laser emitting unit 12 for emitting a second laser beam 23 with a wavelength of $\lambda 2$. The wavelength $\lambda 1$ and the wavelength $\lambda 2$ are different in wavelength from each other. In the present embodiment, there is a relation of $\lambda 2 > \lambda 1$. For instance, a laser beam is used, which has 395 nm as $\lambda 1$ and 415 nm as $\lambda 2$.

The first laser beam 22 emitted from the laser emitting unit 11 is converged and projected to a point to be inspected on a substrate 5 via an optical path switching means 24, a first lens unit 25, a first projecting mirror 26, a second projecting mirror 27, and a projecting lens 28. The first lens unit 25, the first projecting mirror 26, the second projecting mirror 27, and the projecting lens 28 are arranged so as to constitute a first projection optical axis 29.

The second laser beam 23 emitted from the second laser emitting unit 12 is converged and projected to a point to be inspected on the substrate 5 via the optical path switching means 24, a second lens unit 30, a third projecting mirror 31, a fourth projecting mirror 32, and the projecting lens 28. The second lens unit 30, the third projecting mirror 31, the fourth projecting mirror 32, and the projecting lens 28 are arranged so as to constitute a second projection optical axis 33.

Figure 2:
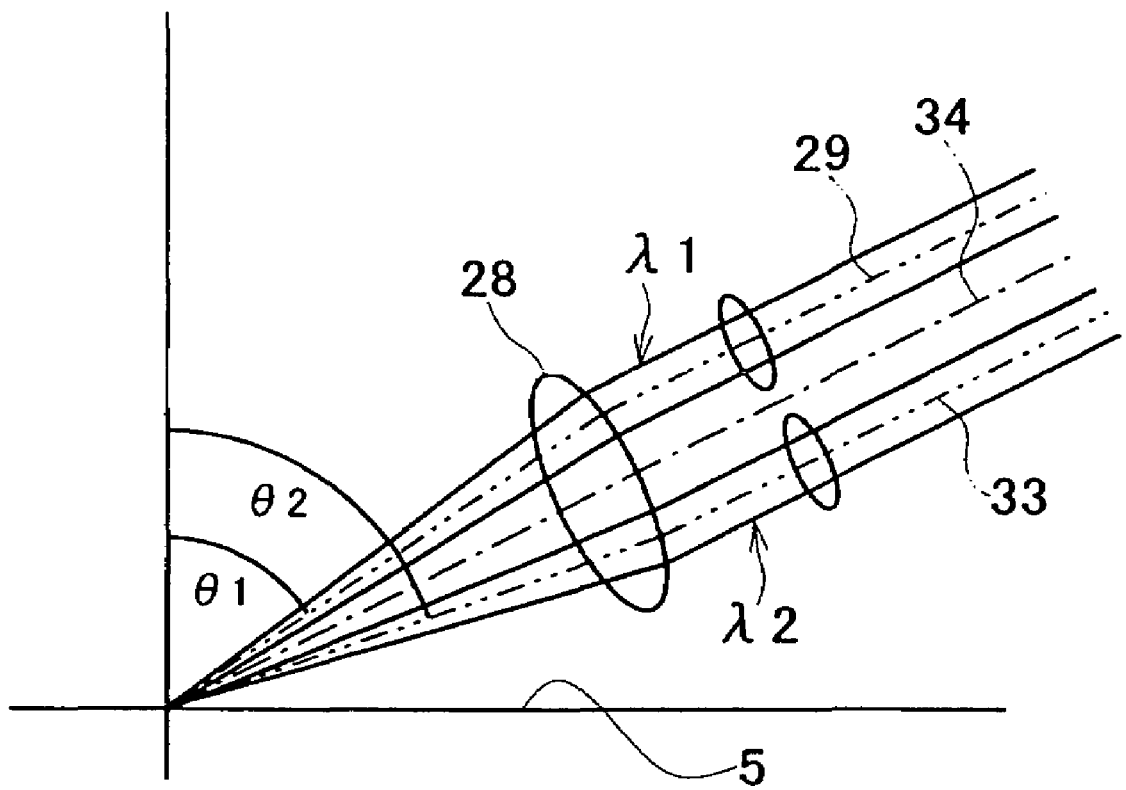
FIG. 2 is a diagram to explain the above embodiment.

The first projection optical axis 29 and the second projection optical axis 33 are running in parallel to a main optical axis 34 of the projecting lens 28 and are separated from each other by a predetermined distance under the standard conditions. When the first projection optical axis 29 and the second projection optical axis 33 run in parallel to each other, the first projection optical axis 29 and the second projection optical axis 33 do not necessarily run in parallel to the main optical axis 34. A luminous flux having the first projection optical axis 29 and a luminous flux having the second projection optical axis 33 are converged to the same point to be inspected on the main optical axis 34. Further, when an incident angle $\theta 1$ of the first projection optical axis 29 to the substrate 5 is compared with an incident angle $\theta 2$ of the second projection optical axis 33 to the substrate 5, the incident angle $\theta 2$ of the second projection optical axis 33 is larger (See FIG. 2). (The angles $\theta 1$ and $\theta 2$ each represents an angle with respect to a line perpendicular to the substrate 5.)

It is preferable that the incident angle $\theta 1$ and the incident angle $\theta 2$ are set so as to have larger angular difference, and that the first projection optical axis 29 and the second projection optical axis 33 are set so as to be present on the same plane running perpendicular to the substrate 5.

When the laser beams 22 and 23 having different wavelengths are projected to the substrate 5 at the incident angle $\theta 1$ and at the incident angle $\theta 2$ respectively, the incident angle $\theta 1$ and the incident angle $\theta 2$ are set in such manner that intensities of the reflected scattered lights detected by fluctuation of reflectivity caused by film thickness are complementary to each other with respect to the laser beams 22 and 23 having different wavelengths respectively. For instance, when the wavelength of the first laser beam 22 is 395 nm and the wavelength of the second laser beam 23 is 415 nm, it is preferable that the incident angle $\theta 1$ is 64.5° and the incident angle $\theta 2$ is 74.6°.

Figure 3:
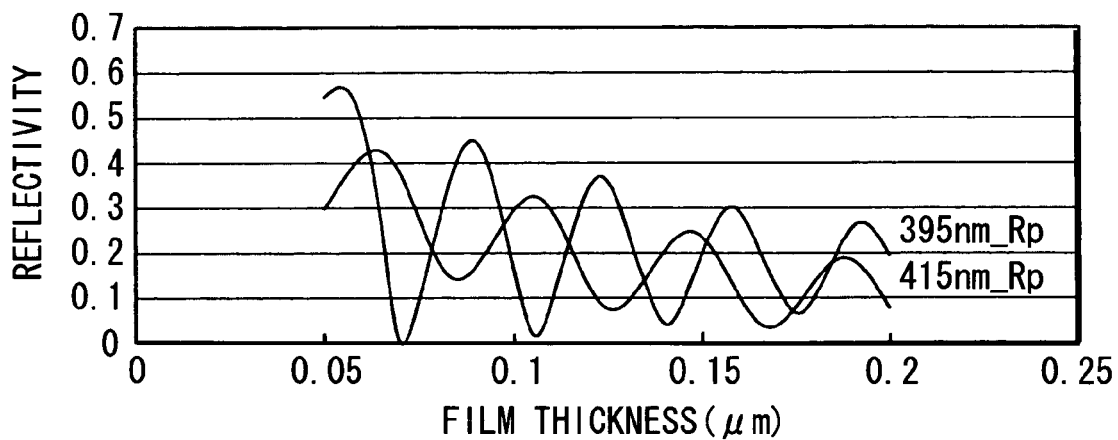
FIG. 3 is a diagram showing fluctuation of reflectivity associated with variation of film thickness on substrate surface when wavelengths of the light beams are different.

Even when the type of the film is the same, the reflectivity is fluctuated when the film thickness is varied as described above. Further, when the wavelengths are different, the reflectivity is fluctuated with approximately the same cycle with the film thickness within the range of 0.05μ–0.2μ for each wavelength, while the phase of the fluctuation cycle is deviated. FIG. 3 shows the aspect of fluctuation of the reflectivity when the laser beam is projected to the substrate under the condition that the laser beams 22 and 23 of p-polarized light with a wavelength $\lambda 1$ of 395 nm and a wavelength $\lambda 2$ of 415 nm respectively are projected with an incident angle $\theta 1$ of the first laser beam 22 with the wavelength $\lambda 1$ at smaller angle and with an incident angle $\theta 2$ of the second laser beam 23 of the wavelength $\lambda 2$ at larger angle. The reflectivity shows the similar fluctuation when the laser beams of s-polarized light are projected.

By designing in such manner that the wavelength $\lambda 1$ and the wavelength $\lambda 2$ have a difference of about 20 nm between them so as to be near wavelengths, the cycles of fluctuation of the reflectivity are deviated each other by about $\pi/2$ so that the maximum value and the minimum value of these two values of reflectivity are approximately overlapped on each other. By setting the incident angle $\theta 1$ of the laser beam with the wavelength $\lambda 1$ (395 nm) to 64.5° and by setting the incident angle $\theta 2$ of the laser beam with the wavelength $\lambda 2$ (415 nm) to 74.6°, the maximum values of the reflectivity of the reflected scattered light is approximately equal with each other between the two laser beams.

Figure 4:
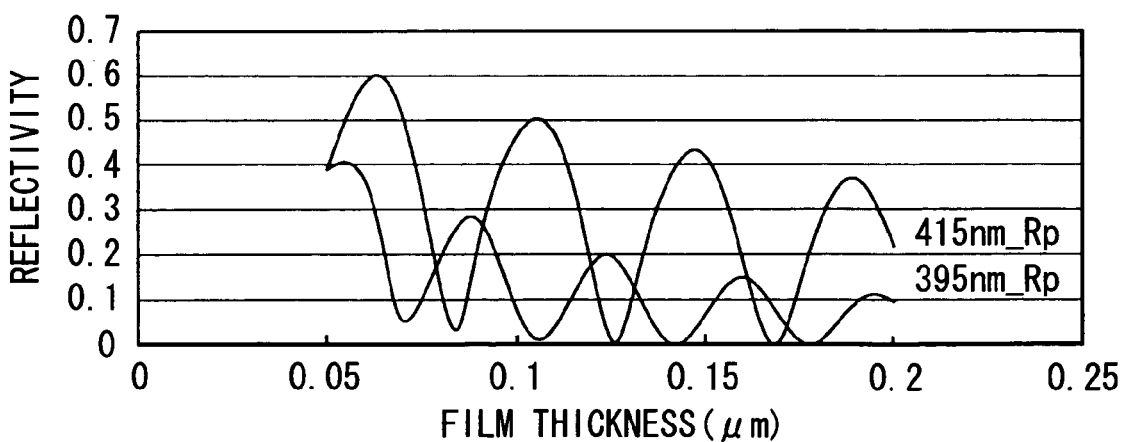
FIG. 4 is a diagram showing fluctuation of reflectivity associated with variation of film thickness on substrate surface when wavelengths of the light beams are different.

FIG. 4 shows a case where the incident angle $\theta 2$ of the laser beam with longer wavelength is set to a higher value and the incident angle $\theta 1$ of the laser beam with shorter wavelength is set to a lower value. This specifically shows the difference of the maximum values of the reflectivity of the reflected scattered light. In this case, also, the maximum value and the minimum value of the reflectivities of the two laser beams approximately overlap on each other. By individually controlling the intensities of the laser beams 22 and 23 emitted from the first laser emitting unit 11 and the second laser emitting unit 12 respectively and by adjusting the light amount, it is possible to set the intensities of the reflected scattered lights of the two laser beams to the same value or approximately the same value.

Now, description will be given on operation.

The first laser emitting unit 11 and the second laser emitting unit 12 are operated independently from each other and can emit the laser beams independently from each other. The emitting conditions such as emission intensity are controlled by the control unit 6. By the optical path switching means 24, it is possible to select whether the first laser beam 22 emitted from the first laser emitting unit 11 should be projected to the substrate 5 via the first projection optical axis 29 or via the second projection optical axis 33. Similarly, by the optical path switching means 24, it is possible to select whether the second laser beam 23 emitted from the second laser emitting unit 12 should be projected to the substrate 5 via the second projection optical axis 33 or via the first projection optical axis 29. Specifically, by changing an incident position to the projecting lens 28 by means of the optical path switching means 24, it is possible to change the incident angle to the point to be inspected (on the substrate surface).

Further, the first laser beam 22 and the second laser beam 23 can be projected to the point to be inspected at the same time from the first laser emitting unit 11 and the second laser emitting unit 12. The substrate 5 is rotated by the rotary motor 7 and projecting points of the laser beams 22 and 23 are moved in a radial direction. As a result, the point to be inspected is shifted spirally over the entire surface of the substrate 5.

Depending on the type of the film formed on the substrate 5, adequate inspecting condition can be variously chosen by the selection of the first laser emitting unit 11 or the second laser emitting unit 12 or by the switching of optical path by the optical path switching means 24.

By adequately selecting the each wavelength $\lambda$ and the each incident angle $\theta$ of the each inspection light depending on the type of the film formed on the substrate to be inspected, surface inspection can be carried out without being influenced from the fluctuation of the reflectivity on the substrate surface. If it is designed in such manner that relevant data on the incident angle of a plurality of laser beams with different wavelengths and the reflectivity on the substrate surface are stored in a memory unit which is incorporated or connected to the device and the relevant data is referred according to each substrate to be inspected, it is also possible to set the incident angle to complement the fluctuation of the reflectivity on the substrate surface.

On the other hand, the relevant data of the incident angle of the laser beam and the reflectivity on the substrate surface is also available from external storage unit if the means such as network is used as communication means. The inspection with high accuracy can be performed if new relevant data is available at all times.

Next, description will be given on the surface inspection of a substrate where a thickness of a formed film is varied or such variation is anticipated. When the point to be inspected is shifted over the entire surface of the substrate 5, film thickness at the point to be inspected is varied.

Here, the projecting conditions of the laser beams are set as follows: For the first laser beam 22 with the wavelength $\lambda 1$ (395 nm) and the second laser beam 23 with the wavelength $\lambda 2$ (415 nm), the incident angle $\theta 1$ of the first laser beam 22 is set to 64.5° and the incident angle $\theta 2$ of the second laser beam 23 is set to 74.6°. (The conditions are the same as the projecting condition shown in FIG. 3.)

As shown in FIG. 3, the fluctuations of the values of reflectivity of the first laser beam 22 and the second laser beam 23 are complementary to each other. If the first laser beam 22 and the second laser beam 23 are projected at the same time, and total sum of the reflected scattered light components of both the laser beams 22 and 23 is detected at the photodetector 18, it is possible to suppress the reduction of the reflectivity associated with the variation of film thickness. Even when the film thickness is varied, it is possible to detect the reflected scattered light with necessary intensity.

In the case where the first laser beam 22 and the second laser beam 23 are projected at the same time, it may be designed in such manner that a wavelength separating means such as an optical filter is used at the photodetection unit 3 so as to separately detect the first laser beam 22 and the second laser beam 23. The reflected scattered light component of the first laser beam 22 and the reflected scattered light component of the second laser beam 23 may be compared with each other, and the component with higher value may be regarded as the detection light. In this case, the intensity of the reflected scattered light is turned to an intensity less variable and more stable.

Further, it may be designed in such manner that the emission of the first laser beam 22 from the first laser emitting unit 11 and the emission of the second laser beam 23 from the second laser emitting unit 12 are alternately turned on and off by the optical path switching means 24 at a speed sufficiently higher than the scanning speed of the laser beams 22 and 23 to the substrate 5, and that the reflected scattered light of the first laser beam 22 and the reflected scattered light of the second laser beam 23 can be separately detected by the photodetector 18. As a result, the reflected scattered light components can be compared with each other, and the reflected scattered light component with higher value may be regarded as the detection light. In this case again, the intensity of the reflected scattered light is turned to an intensity less variable and more stable.

In the embodiment described above, the laser beams with two different types were described, while the laser beams with three or more different wavelengths may be used so that the fluctuation of the reflectivity can be complemented between at least two laser beams and the reflected scattered light may be detected. Also, the wavelengths of the laser beams may be set to a value other than 395 nm or 415 nm as given above.

Regarding the maximum value of the reflectivity, if the intensity of the laser beam is adjusted and the intensity of the received reflected scattered light is adjusted, there is no need to change the incident angles of two or more laser beams to the substrate 5.

Further, in the above embodiment, the laser beams 22 and 23 are projected in parallel to the main optical axis 34 of the projecting lens 28 and the incident angles of the laser beams 22 and 23 to the substrate 5 are changed. It may be designed in such manner that the projecting lens 28 may not be used and the second projecting mirror 27 and the fourth projecting mirror 32 may be designed as rotatable, and the incident angle may be changed by adjusting the second projecting mirror 27 and the fourth projecting mirror 32.

The present invention provides a method for surface inspection, which comprises the step of projecting at least two laser beams with different wavelengths to a same point to be inspected via a same projecting lens, the step of setting incident angles of the two laser beams so that fluctuations of values of reflectivity of the laser beams are complementary to each other, and the step of detecting reflected scattered light components. As a result, surface inspection can be carried out with stable and high inspection accuracy without being influenced from the fluctuation of reflectivity caused by the change of thickness of film on the surface of the object to be inspected, which has light transmittance. Also, when there are changes in film thickness on the same substrate, the variation of intensity of the reflected scattered light can be reduced. The variation of the detection accuracy can be suppressed, and this contributes to the improvement of reliability of the surface inspection.

On the other hand, if a plurality of laser beams with different wavelengths are projected with different incident angles to the substrate without changing the incident angle as a projection optical system with the purpose of obtaining stable intensity of the reflected scattered light with respect to the wavelength of the inspection light and to the thickness of the film formed on the substrate to be inspected, it is possible to perform stabilized inspection on any type of substrate where films of different types and thickness are formed.

What is claimed is:

1. A method for surface inspection, comprising the step of projecting at least two laser beams with different wavelengths to a same point to be inspected via a same projecting lens, the step of setting incident angles of the two laser beams so that fluctuations of values of reflectivity of the laser beams are complementary to each other, and the step of detecting reflected scattered light components.

2. A method for surface inspection according to claim 1, wherein said at least two laser beams have different incident angles with respect to the point to be inspected.

3. A method for surface inspection according to claim 1, wherein wavelengths of said at least two laser beams are 395 nm and 415 nm respectively.

4. A method for surface inspection according to claim 1, wherein an incident angle of the laser beam with wavelength of 395 nm is 64.5° and an incident angle of the laser beam with wavelength of 415 nm is 74.6°.

5. A method for surface inspection according to claim 1, wherein the incident angles are set based on the wavelengths of the each laser beams and to a thickness of a film formed on the point to be inspected.

6. A method for surface inspection according to claim 1, wherein the incident angle of each of the laser beams is set according to a type of the film formed on the point to be inspected.

7. A method for surface inspection according to claim 1, wherein said at least two laser beams are projected at the same time and the reflected scattered light components of the two laser beams are detected.

8. A method for surface inspection according to claim 1, wherein said at least two laser beams are projected at the same time, the reflected scattered light components of said two laser beams each are separately detected from the reflected scattered light components of said two laser beams by an optical separating means, and a component with higher detection value is regarded as a detection light.

9. A method for surface inspection according to claim 1, wherein said at least two laser beams are projected alternately, the reflected scattered light components of said two laser beams each are separately detected, and a component with higher detection value is regarded as a detection light.

10. A method for surface inspection according to claim 1, wherein the incident angle of each of said laser beams is respectively determined according to type of the film formed on the substrate.

11. A method for surface inspection according to claim 1, wherein said incident angle is set depending on a substrate to be inspected so that the fluctuations of values of reflectivity of each of the laser beams on the substrate surface are complementary to each other, based on relevant data relating to incident angles of two or more laser beams with different wavelengths and to reflectivity on a substrate surface.

12. A device for surface inspection, comprising at least two laser emitting units for emitting two or more laser beams with different wavelengths independently from each other, a projecting lens for projecting said laser beams to a surface of a substrate, a projecting optical system for projecting said laser beams in parallel to said projecting lens, and an incident position adjusting means for adjusting an incident position to said projecting lens, wherein an incident angle of each of the laser beams to the substrate surface is set by adjusting the incident position of each of the laser beams to said projecting lens so that fluctuations of values of reflectivity of the laser beams are complementary to each other.

13. A device for surface inspection according to claim 12, wherein said device comprises a photodetection unit for receiving reflected scattered light components and a wavelength separating optical means, and wherein a reflected scattered light component corresponding to each laser beam is detected from reflected scattered light components and is compared when two or more different laser beams are projected by said projecting optical system at the same time, and a reflected scattered light component with a higher comparison value is detected as a detection light.

14. A device for surface inspection according to claim 12, further comprising a photodetection unit for receiving reflected scattered light components, wherein said projecting optical system comprises an optical path switching means, and wherein a projection laser beam is selectively projected by the switching of optical path by said optical switching means, reflected scattered light components of each of the laser beams are separately detected, the each reflected scattered light components are compared with each other, and a reflected scattered light component with a higher comparison value is detected as a detection light.

15. A device for surface inspection according to claim 12, wherein wavelengths of said two or more laser beams are 395 nm and 415 nm respectively.

16. A device for surface inspection according to claim 15, wherein the incident angle of the laser beam with a wavelength of 395 nm is 64.5° and the incident angle of the laser beam with a wavelength of 415 nm is 74.6°.

* * * * *